United States Patent [19]

Lee et al.

[11] Patent Number: 5,919,976
[45] Date of Patent: Jul. 6, 1999

[54] SULFONATED ALIPHATIC COMPOUNDS

[75] Inventors: Bin Lee, Coraopolis, Pa.; Harold Pielartzik, Krefeld; Gundolf Jacobs, Rosrath, both of Germany

[73] Assignee: Bayer Corporation, Pittsburgh, Pa.

[21] Appl. No.: 08/986,702

[22] Filed: Dec. 8, 1997

Related U.S. Application Data

[63] Continuation-in-part of application No. 08/660,664, Jun. 5, 1996, abandoned, which is a continuation of application No. 08/129,212, Sep. 29, 1993, abandoned, which is a continuation-in-part of application No. 08/041,116, Apr. 1, 1993, abandoned.

[51] Int. Cl.$^6$ .................................................. C07C 61/00
[52] U.S. Cl. ................................................ 562/120
[58] Field of Search ................................................ 562/120

[56] References Cited

FOREIGN PATENT DOCUMENTS

| | | | |
|---|---|---|---|
| 682207 | 11/1952 | Germany | 514/1 |
| 154093 | 2/1962 | Germany | 514/1 |

OTHER PUBLICATIONS

Database WPIDS on STN, Sanyo Chem, AN 74–18566V, "Butadiene (co)polymer sulphonates prodn . . . ", JP 49006834 B, Feb. 16, 1974.

Databse CAPLUS on STN, Fujimoto et al, AN 1975:17521, "Sulfonates of Butadiene polymer, copolymers or derivatives thereof", JP 49006834, Feb. 16, 1974.

*Primary Examiner*—Keith D. MacMillan
*Attorney, Agent, or Firm*—Joseph C. Gil; Aron Preis

[57] ABSTRACT

A process for incorporating sulfonic acid groups in the structure of an aliphatic, non-polar, water insoluble compound is disclosed. In the process the compound is first dissolved in an appropriate solvent and is then reacted in the presence of a catalyst and oxygen with an aqueous sulfite solution. The sulfonation renders the compound polar and water absorbent and, therefore, suitable in a variety of applications.

6 Claims, No Drawings

SULFONATED ALIPHATIC COMPOUNDS

This application is a Continuation in Part of application Ser. No. 08/660,664 filed Jun. 5, 1996, now abandoned which is a Continuation of Ser. No. 08/129,212 filed Sep. 29, 1993, now abandoned which is a Continuation in Part of U.S. application Ser. No. 08/041,116, filed Apr. 1, 1993, now abandoned.

FIELD OF THE INVENTION

The invention relates to an aliphatic compound which contains sulfonic acid groups and a process for its preparation.

SUMMARY OF THE INVENTION

A process for incorporating sulfonic acid groups in the structure of an aliphatic, non-polar, water insoluble compound is disclosed. In the process the compound is first dissolved in an appropriate solvent and is then reacted in the presence of a catalyst and oxygen with an aqueous bisulfite solution. The sulfonation renders the compound polar and water absorbent and, therefore, suitable in a variety of applications.

BACKGROUND OF THE INVENTION

Polybutadiene polyol has been commercially available and used in a variety of applications. Despite its many interesting properties which are associated with the aliphatic backbone, polybutadiene polyol found only limited applicability in polyurethane applications. The hydrophobic, non-polar backbone imparts excellent hydrolytic stability, good resistance to aqueous inorganic acids and bases, stain resistance, internal mold release properties, good adhesion to non-polar polyolefin substrates and good electrical insulation properties to polyurethane products. However, because of its non-polar characteristics, polybutadiene polyol encounters incompatibility in mixtures with most of the conventional polyether or polyester polyols. In addition, the low dispersibility in aqueous media excludes its use in the formulations of aqueous polyurethane dispersions. The technical problem addressed by the work leading up to the present invention aimed at modifying the polybutadiene polyol to render it more polar and hence more useful in polyurethane applications.

The relevant art is noted to include U.S. Pat. No. 4,048,221 which disclosed adding bisulfites to alkoxylated dihydroxy alkenes to produce dihydroxy sulfonates containing ether groups in a process entailing a reaction with a bisulfite in an aqueous medium. A similar reaction has been disclosed in U.S. Pat. No. 4,056,564.

The art also reported the preparation of polybutadiene backboned ionomers having sulfate salt terminal groups. Hegedus et al in J. Polym. Sci., Part A: Polym. Chem., 26(2), 367–80, 1988 disclosed that the solubility characteristics of the sulfate-terminated hydrogenated polybutadiene oligomers have been shifted towards a preference for polar solvents by the presence of salt groups. Also noted are U.S. Pat. Nos. 4,920,179 and 5,023,005 which disclosed reacting a sulfone derivative of maleic anhydride with an unsaturated organic compound to produce sulfone polymers. Aliphatic polyesters containing sulphur in the form of sulphide or disulphide groups in both the acid component and the diol component, and a process for their preparation has been disclosed in U.S. Pat. No. 4,699,972. Sulfonation of oligomers by sodium bisulfite has also been disclosed by Yilgor et al. in "Novel Reactive Polyether Oligomers Via Ring-Opening Polymerization and Their Use"—Polymer Reprints, Vol. 31, number 1,75, April 1990. The thus sulfonated ethers are said to be usefully incorporated into polyurethanes.

DETAILED DESCRIPTION OF THE INVENTION

The process in accordance with the present invention results in the incorporation of sulfonic acid groups in the structure of an aliphatic, non-polar, water insoluble compound. In the context of the invention, sulfonic acid groups refer to sulfonic acid and/or sulfonates (neutralized sulfonic acid) groups. The process entails the following steps:

(i) dissolving the compound in a water soluble solvent having a boiling temperature in the range of 60 to 250° C. to produce the first solution, and (ii) reacting the first solution with an aqueous solution of a sulfonation agent in the presence of a catalyst and oxygen to produce the sulfonated product and (iii) isolating the sulfonated product.

The compound to be sulfonated in accordance with the process of the invention is a non-polar, water-insoluble aliphatic compound which contains at least 1 mole % unsaturation. The compound has a number average molecular weight in the range of about 500 to 20,000, and a functionality of about 0 to 10, preferably 0 to 3. Functionality, in the present context, refers to the number of reactive end groups per molecule. The compound may be hydrogen-terminated or in the alternative it may have reactive end-groups such as $NH_2$, COOH, or OH. Preferably the compound to be sulfonated is based on polybutadiene, most preferably it is polybutadiene polyol. Polybutadiene polyol is generally consisting of a mixture of three isomers, the relative amounts of which in the mixture depends on the method of their preparation. The process of the invention is applicable to all isomers and their combinations. Suitable commercially available polybutadiene oils have been disclosed by H. D. W. Zagefka in Crosslinking Reactions of Modified Polybutadienes; Advances in Organic Coatings Science & Technology, Vol. 12, 1990 pp.58 et seq., which is incorporated herein by reference.

The suitable solvent entailed in the process of the invention is one which in addition to its function as a solvent for the compound to be sulfonated, needs to be water soluble and have a boiling temperature in the range of 60 to 250° C. Examples of suitable solvents include DMAC (N,N-dimethylacetamide having a boiling point of about 165° C.,) DMSO (dimethyl sulfoxide, boiling point 189° C.,) NMP (N-methylpyrrolidone, having a boiling point of 202° C.), DMF and dioxane. The preferred solvent is selected among DMF and dioxane.

The sulfonation agent useful in the present invention conforms to $$MHSO_3$$

where M denotes H, Na, Li, K or $NH_4$. Preferably, the agent is sodium bisulfite. A commercial product in the form of an aqueous solution containing about 38 to 43 percent by weight of bisulfite has been used successfully in carrying out the process of the invention.

The process is best carried out in the presence of a catalytic amount of peroxide or oxygen. Atmospheric oxygen is sufficient for facilitating the reaction. The process is characterized in that (cyclo)aliphatic nitro compound is not a reactant.

The reactants, the compound in solution in an appropriate solvent is mixed with the aqueous solution of the sulfonation agent and the mixture heated to about 100–110° C. Upon completion the reaction mixture is vacuum distilled and washed with water. The cooled and washed product is then filtered to separate out any unreacted sulfonation agent and then dried.

The product, the sulfonated compound, containing 0.1 to 30 percent by weight of sulfonate groups, is sufficiently polar and thus miscible in polyester polyols or polyether polyols. Moreover, the sulfonated compound thus produced is characterized in, among others, that it is capable of absorbing water to an extent amounting to at least three times its own weight.

The process of the invention also has the beneficial effect of ridding commercially available polybutadiene polyols of their associated unpleasant odor. The offensive residual content (600–800 ppm) of vinyl cyclohexane, a by-product of the polymerization of butadiene is reacted with the sulfonation agent to produce a non-volatile (and thus non-offensive) product which may be washed off with water.

The invention is further illustrated but is not intended to be limited by the following examples in which all parts and percentages are by weight unless otherwise specified.

EXAMPLES

Example

Materials used:
- 20 gallons of polybutadiene polyol—number average MW about 2800 (Poly bd 45HT, a product of Atochem North America, Inc.)
- 6.82 kg of sodium bisulfite (from Aldrich Inc.)
- 48 gallons of DMF, and
- 3.7 gallons of distilled water.

Procedure:

Into a 100 gallon-size reactor there were introduced 32 gallons of DMF and the temperature raised to about 95–105° C. 20 gallons of polybutadiene polyol were then introduced to the reactor while stirring. Caution is advised relative to the offensive odor of the polyol. A clear solution results, the clarity is critically dependent on the temperature and concentration. While at the noted temperature sodium bisulfite in the form of water solution is added while stirring and a viscous, milky white dispersion results. The solution viscosity increases steadily during the course of the reaction. After 1 hour at that temperature there is added the remaining (16 gallons) DMF to reduce the solution viscosity. This is to facilitate good mixing and stirring. It is important to carry out the reaction in the presence of atmospheric air as the reaction requires some oxygen. The solution remains heterogeneous, having milky white appearance throughout the reaction. It should be noted that the presence of excessive amounts of oxygen will cause undesired oxidation of sodium bisulfite to the corresponding bisulfate which is unreactive with polybutadiene. Excess oxygen would, therefore, cause increased turbidity (haziness) of the final product.

The reaction continues at the above noted temperature for an additional eight hours and the solution appears as a viscous milky white liquid.

The DMF and water were then vacuum distilled, while additional water may be added, if necessary, to assist in removing trace amounts of the DMF at the later stages of the distillation. Any un-removed solvent in the material will cause turbidity.

The product, which is a clear viscous liquid with slight haziness, is then collected. Elemental analysis of the product confirmed 90–95% of targeted sulfonation. Toluene may be used for cleaning up the reactor.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for incorporating sulfonic acid groups in the structure of an aliphatic, non-polar, water insoluble compound having a number average molecular weight range of about 2000 to 18,000, and a functionality of about 0 to 10, comprising, (i) dissolving said compound in a water soluble solvent having a boiling temperature in the range of 60 to 250° C., selected from the group consisting of DMAC, DMSO, NMP, DMF and dioxane to produce first solution (ii) reacting said first solution with an aqueous solution of a sulfonation agent in the presence of oxygen, said agent confirming to

MHSO$_3$ where M denotes H, Na, Li, K or NH$_4$ to produce sulfonated product and (iii) isolating said product said process characterized in that (cyclo)aliphatic nitro compound is not a reactant.

2. The process of claim 1 wherein said compound contains polybutadiene structural units.

3. The process of claim 2 wherein said compound is end-terminated by at least one member selected from the group consisting of —H, —NH$_2$, —COOH, and —OH.

4. The process of claim 1 wherein said compound is polybutadiene polyol.

5. The product prepared by the process of claim 1.

6. The product prepared by the process of claim 4.

* * * * *